United States Patent
Knight et al.

(10) Patent No.: US 9,713,778 B2
(45) Date of Patent: Jul. 25, 2017

(54) COUNTERCURRENT CHROMATOGRAPHY ROTOR

(71) Applicant: CC Biotech LLC, Rockville, MD (US)

(72) Inventors: Martha Knight, Washington, DC (US); Thomas Finn, Rockville, MD (US)

( * ) Notice: Subject to any disclaimer, the term of this patent is extended or adjusted under 35 U.S.C. 154(b) by 541 days.

(21) Appl. No.: 14/093,481

(22) Filed: Dec. 1, 2013

(65) Prior Publication Data

US 2014/0091036 A1 Apr. 3, 2014

Related U.S. Application Data

(62) Division of application No. 13/129,811, filed as application No. PCT/US2009/064976 on Nov. 18, 2009, now Pat. No. 8,597,509.

(Continued)

(51) Int. Cl.
*B01D 15/08* (2006.01)
*G01N 30/42* (2006.01)
(Continued)

(52) U.S. Cl.
CPC .......... *B01D 15/1807* (2013.01); *G01N 30/42* (2013.01); *B33Y 80/00* (2014.12); *Y10T 137/0402* (2015.04)

(58) Field of Classification Search
CPC .................................................... G01N 30/42
See application file for complete search history.

(56) References Cited

U.S. PATENT DOCUMENTS 4,894,152 A 1/1990 Colvin
5,104,531 A * 4/1992 Ito .......................... G01N 30/42
210/198.2

(Continued)

FOREIGN PATENT DOCUMENTS

CN 201143392 11/2008
WO WO2004085020 10/2004

OTHER PUBLICATIONS

Y. Ito, R. Clary, J. Powell, M. Knight, T. Finn. "Improved spiral tube assembly for high-speed counter-current chromatography" J Chromatogr A, doi:10.1016/j.chroma.2008.10.126, first published online Nov. 13, 2008.*

(Continued)

*Primary Examiner* — Krishnan S Menon
*Assistant Examiner* — Ryan B Huang
(74) *Attorney, Agent, or Firm* — MDIP LLC

(57) ABSTRACT

A method for constructing a spiral tube support apparatus used in countercurrent chromatography, improvements to countercurrent chromatography tube support design, and methods of using the improved countercurrent chromatography apparatus are described. The spiral tube support apparatus may be constructed by a shape forming process such as a three dimensional printing process that in turn uses a laser sintering technique, and can be made out of any easily formed material. Shape changes on both the tube support and the top improve the performance of the tube support and ease of manufacturing. The improved tube support and new method of creation permit use in both micro or macro scale preparations and use in small or large molecule preparations. In particular, specific solvent systems are described that permit purification of proteins.

10 Claims, 5 Drawing Sheets

Related U.S. Application Data

(60) Provisional application No. 61/199,587, filed on Nov. 18, 2008.

(51) Int. Cl.
  *B01D 15/18* (2006.01)
  *B33Y 80/00* (2015.01)

(56) References Cited

U.S. PATENT DOCUMENTS

| | | |
|---|---|---|
| 5,143,630 A | 9/1992 | Rolchigo |
| 5,993,674 A | 11/1999 | Rolchigo |
| 6,296,749 B1 | 10/2001 | Balch et al. |
| 7,892,847 B2 | 2/2011 | Ito |
| 2005/0242040 A1* | 11/2005 | Ito ................ B01D 15/1807 210/658 |
| 2006/0052755 A1* | 3/2006 | Lim ................ A61M 25/0637 604/263 |
| 2006/0243650 A1 | 11/2006 | Gebauer |
| 2006/0253076 A1* | 11/2006 | Butts ............... A61M 39/0247 604/167.06 |
| 2010/0276351 A1 | 11/2010 | Ito |

OTHER PUBLICATIONS

Ito et al. "Improved spiral tube assembly for high-speed counter-current chromatography" J Chromatogr A, May 18, 2009; 1216(19): 4193-4200. Published online Nov. 13, 2008. doi: 10.1016/j.chroma. 2008.10.126.*

* cited by examiner

COUNTERCURRENT CHROMATOGRAPHY ROTOR

FIELD OF THE INVENTION

The invention consists of a method for constructing, a method for using, and an improved design of a spiral tube support apparatus for use in countercurrent chromatography (CCC).

BACKGROUND OF THE INVENTION

Chromatography is a technique whereby a substance dissolved in a mobile phase is passed through a stationary phase to separate the substance so that it may be purified or identified, often from a complex mixture of substances. A substance includes, but is not limited to: (1) gases, (2) chemicals, (3) biological materials such as DNAs, carbohydrates, lipids, peptides, proteins or combinations thereof, (4) molecules, or (5) any combination of the aforementioned substances. A substance separated using chromatography may be analyzed by various means of detection which may be attached to the apparatus. Many variations in both the type of chromatography and the mechanism of separation presently exist and are actively used in research.

Countercurrent chromatography is based on liquid-liquid partitioning where both the mobile and stationary phases are in a liquid state. The technique separates compounds in a moving liquid phase from a stationary liquid phase held in coiled tubing and exposed to forces arising by rotation, for example, in a planetary centrifuge. Countercurrent chromatography has existed since the early 1970's and has been successfully employed to separate chemical compounds or small molecule substances. U.S. Pat. Nos. 3,784,467, 3,775,309, 6,503,398, 5,770,083, 5,354,473, 5,332,504 and 5,215,664. Sample substances are separated according to the solubility of the substances between the phases. Solvents may be mixed in varying volume ratios to form two stable immiscible phases that comprise the solvent system for the chromatography. Countercurrent chromatography provides a versatile method of separating or purifying small molecule substances; indeed, the prior art has been largely limited to small molecule separation, identification, or purification. While a few prior disclosures relate to countercurrent chromatography centrifuges that are alleged to separate large molecule substances, those lacked the ability to do so as efficiently and well as the instant invention. U.S. Pat. Nos. 4,714,554 and 5,104,531.

The earliest embodiment of countercurrent chromatography involved a series of columns fixed vertically and connected to one another by transfer tubing with a pump at one end. U.S. Pat. No. 3,784,467. The sample substance was dissolved in a mixture of the solid and stationary phases in another column that was then connected to the pump by transfer tubing and placed before the other columns in the series.

A subsequent invention showed how to configure continuos tubing for solvent entry and exit, without a rotating seal, in helical coils that rotate around a central axis, U.S. Pat. No. 3,775,309. In one revolution, the apparatus accomplished a twisting and untwisting action in a planetary motion that mixed the phases. During a single revolution in that system, inside a tubing coil filled with a dual phase solvent, the lighter phase migrates to one end (head) and the heavier phase migrates to the other end (tail) depending on (1) the rotational direction of the coil (clockwise or counterclockwise) and (2) the rotational direction of the rotor (clockwise or counterclockwise). The mobile phase is pumped into the end against the direction in which the stationary phase prefers to move; thus, the stationary phase at equilibrium is retained at 40-80% of the total volume of the coil. Excess of the mobile phase elutes out the other end. Current embodiments or applications of planetary CCC centrifuges involve different orientations of the helical tubing. U.S. Pat. Nos. 3,994,805, 4,430,216, 4,532,039 and 4,714,554.

In recent years, the helical tubing or spool has been replaced by spirally-organized tubing held in place by a frame called a spiral tubing support. U.S. Pat. Pub. No. US 2005/0242040. Presently, construction of the spiral tubing support is slow and laborious. The first type of that apparatus was built by crafting spiral channels ground two inches deep into light aluminum and radial channels to hold Teflon® tubing wound in four spirals in one plane. The advantages of the spiral tubing support are (1) lack of leakage through sandwiched plates with flow channels and (2) higher resolution of substances due to the smaller diameter of the tubing.

SUMMARY OF THE INVENTION

In one embodiment, the invention comprises a countercurrent chromatography apparatus comprising one or more first surfaces, wherein said first surface comprises a plurality of spiral channels or grooves to house a tubing. The first surface optionally contains one or more radial channels. The first surface contains an inlet or outlet, or access port for tubing. The apparatus may additionally comprise one or more of the following improvements: (1) one or more curved radial channels, (2) one or more protrusions in a channel or groove to hold tubing in place, (3) one or more spaces in which weights may be placed, (4) one or more compression screw unions that may be held on by snap locks, (5) one or more retainer supports, and (6) one or more loop structures on the outside of a surface to help guide flow tubing. The term "loop" includes other shapes which may be capable of holding tubing on the outside of the first surface, for example hooks. Radial channels may be curved at one or both ends and in any direction. The first surface may also receive an application or coating of a lubricant, Teflon®, Parylene or liquid polyethylated glycol, on the top to protect tubing from abrasion.

A method for manufacturing a countercurrent chromatography apparatus is also provided. In one embodiment the method comprises one or more first surfaces, wherein said first surface comprises a plurality of spiral channels or grooves. The first surface may be formed using a shape-forming process. The preferred method uses a three-dimensional prototyping machine and a material that can be easily molded. Other possible shape-forming processes that could be used include any type of molding, drilling, machining prototyping, or any combination of the aforementioned processes. A material that can be easily molded includes, but is not limited to one or more of the following: (1) nylon polymer, (2) plastic, (3) polytetrafluoroethylene (Teflon®), (4) polyvinyl chloride, (5) polystyrene, (6) polyamide PA-220, (7) photopolymer, (8) FullCure® material, (9) Polyjet 3D Printer® material, (10) monomeric powder, and (11) a particulate or powder comprising a metal or a metal composite. The three-dimensional prototyping machine may make use of one or more processes to form a layer comprising the first surface such as laser sintering, ultraviolet irradiation, drilling, machining, or prototyping.

The method of manufacturing may further be used to create a first surface comprising one or more of the following improvements: (1) one or more straight radial channels (2) one or more curved radial channels, where curved includes a sinusoidal configuration, an "S" configuration, a reversed "S" configuration and so on, for example, to facilitate tubing placement and seating, for example, to avoid bends and crimps in the tubing, (3) one or more inlets or outlets, or access ports for tubing, (4) one or more spaces or storing means in which weights may be placed, (5) one or more spaces through which a second surface may be attached, (6) one or more threads which may be used to attach an opposing surface, (7) one or more loops to hold tubing, (8) one or more compression screw unions attached by a snap locks for holding a compression screw union, (9) one or more retainer supports, and (10) one or more gears, as well as well as combinations thereof. By combination is meant having more than one of the 10 types of improvements or having a structure carrying at least two of the functions of the individual improvement types. The term "gears" as used herein includes embodiments where one or more gears are (1) directly or indirectly attached to one or more surfaces, (2) attached to a central shaft, (3) included within the bearing block, or (4) any or all combinations of the aforementioned gear positions. The radial channels may be curved at one or both ends and in any direction. Additionally, the method of manufacturing may be used to create a first surface containing a central space through which a shaft may be placed. The first surface can comprise walls at the periphery to form a space for accepting tubing.

The method of manufacturing, in another embodiment, may be used to create a plurality of layers which form a second surface which is the top to the first surface. "Top" includes any surface that acts as a cover, a lid, or any other attachment to the first surface. The second surface may be formed from the same materials as the first surface and using a shape-forming process, such as, a three-dimensional prototyping machine. The three-dimensional prototyping machine may make use of one or more processes to form the layers comprising the second surface including laser sintering, ultraviolet irradiation, drilling, machining, injection molding or prototyping. The method of manufacturing may further be used to create a second surface comprising one or more of the following: (1) an inlet or an outlet, or an access port for tubing, (2) one or more spaces in which weights may be placed, (3) one or more spaces or means through which said first surface may attach, (4) one or more threads which may be used to attach to an opposing surface, (5) one or more loops or hooks to hold tubing, (6) one or more compression screw unions attached by snap locks, and (7) one or more retainer supports, as well as a combination thereof. By combination is meant having more than one of the 7 types of items or having a structure carrying at least two of the functions of the individual types of items. Additionally, the method may be used to create a second surface that attaches to the first surface by one or more of the following: (1) one or more latches, (2) one or more bolts, (3) one or more snaps, (4) one or more clips, (5) one or more notches, (6) one or more central spaces through which a shaft may be placed, (7) one or more threads which may be used to attach an opposing surface, or (8) any known locking mechanisms. For example, threads enable use of screws to a affix the second surface to the first surface. The second surface also can include a means to orient or to affix the second surface to or on the first surface. An example is a shaped protrusion on one of said first or second surface, with a void on the other surface into which said shaped protrusion fits. Generally, the planetary gearing means is attached directly or indirectly to an external surface, such as at the second surface, to enable integration of the rotor of interest into a CCC device as a design choice.

In another embodiment, a method of performing countercurrent chromatography to separate substances is provided that employs an apparatus manufactured by or containing one or more of the aforementioned improvements. "Substances" as used herein includes chemical substances, small organic molecules and biological materials such as DNA, polynucleotides, oligonucleotides protein, polypeptides, polysaccharides, lipids, combinations thereof and so on. The method of performing the countercurrent chromatograph comprises (1) providing a test sample and solvent system, (2) routing tubing through an inlet, spiral and radial channels and an outlet, (3) loading said test sample into said solvent system, (4) placing said combined test sample and solvent system into the apparatus, and (5) rotating the apparatus in a centrifuge for a period of time and at a specified speed. Any type of flexible tubing may be used including, but not limited to: (1) Teflon®, (2) fluorinated ethylene propylene, (3) silicone, (4) stainless steel, (5) Tygon®, (6) crenellated, (7) convoluted, (8) any commonly used flexible tubing, or (9) any tubing that includes a combination of any of the aforementioned materials. The tubing also can be one which has an irregular or non-uniform inner surface. The irregularities can be obtained by using a commercial tubing manufactured in that manner or by manually manipulating the tubing, such as by crimping the tubing, bending the tubing, folding the tubing and so on, to form an introduced imperfection in the tubing, and particularly by disrupting the smooth inner surface of the tubing to form a non-uniform or irregular inner surface in the tubing. The method of performing the countercurrent chromatography may be done with a second surface to cover or to attach to the first surface. The second surface may have a hole for tubing that exits to a central shaft. The method may further include the application or coating of Teflon®, liquid polyethylated glycol, or similar material on either the first or second surface wherever tubing is likely to encounter any type of friction or abrasion. The manufactured apparatus may be used in any type of centrifuge. A preferred type of centrifuge provides for a planetary rotation. In another embodiment, the countercurrent chromatography may be performed with an apparatus containing one or more of the following, improvements: (1) one or more curved radial channels, (2) one or more protrusions in the spiral channels of said apparatus to help guide and seat tubing, (3) one or more retainer supports, and (4) one or more loops on either the spiral tube support surface or the top to guide and seat tubing. The spiral tube support may also require one or more weights for balance; the weights can be placed in one or more spaces in either the first surface, second surface, or both the first and second surface. The method could also involve routing tubing through one or more loops on the first or second surface or both.

The spiral tube support manufactured by the method claimed herein can be used to separate one or more chemical substances, including biological materials. The biological material or chemical substance may be small or large molecules such as DNA, proteins, or peptides. The prior art describes the use of a polar solvent to purify large molecule compounds. Solvent systems that can be used include, but are not limited to the following: (1) two-phase aqueous polyethylene and salt solutions; (2) two-phase heavy alcohol aqueous solutions; (3) PEG (MW 1000) 12.5%-$K_2HPO_4$ 12.5%; or a 1:1 (v/v) solution of sec-butanol-1% trifluoroacetic acid.

BRIEF DESCRIPTION OF THE FIGURES

The following description of the figures and the respective drawings are non-limiting examples that depict various embodiments that exemplify the present invention.

DETAILED DESCRIPTION OF THE INVENTION

A detailed description and various embodiments of the present invention will now be given with reference to the accompanying figures, wherein like numerals describe like elements. The present invention offers several advantages and improvements over the prior art and obviates the shortcomings of the prior art. Although the present invention relates primarily to the field of countercurrent chromatography, the scope of the invention is not limited to such particular (1) methodologies, (2) applications, (3) uses, or (4) or apparatus shapes. Description of specific embodiments of the invention are intended to be one of many possible embodiments of the invention and not intended to be interpreted as limiting or restricting the scope of the invention. Unless otherwise defined, scientific terms used herein have a meaning as would be commonly understood by a person having ordinary skill in the art. It is also understood that plural reference is included, unless the context clearly dictates otherwise. For example, forms such as "a", "an" and "the" are meant to include both the singular and plural as known in the art.

The subject invention may be used in various types of centrifuges including, but not limited to: (1) planetary, (2) fixed angle, (3) swinging bucket, (4) analytical, (5) preparative, and (6) haematocrit. The subject invention may also be operated at a variety of temperatures and may be scaled for applications from small to industrial.

Figure 1:
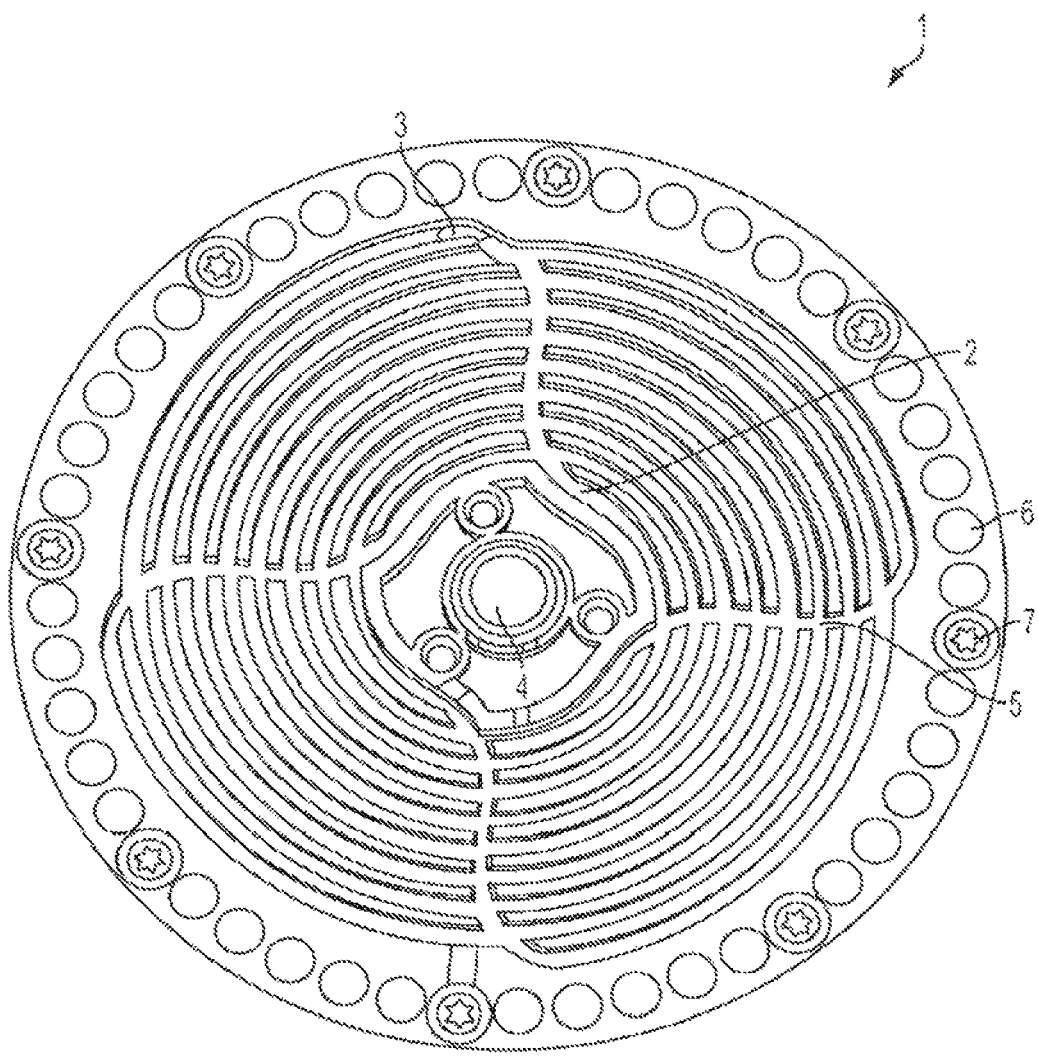
FIG. 1 is a cross-section of the improved spiral tubing support.

In one embodiment, the countercurrent chromatography apparatus is comprised of a plurality of interweaved spiral channels. In one embodiment, equally spaced cuts form radial grooves or channels. The number of equally spaced cuts can include two cuts, three, cuts, four cuts, five cuts and so on. FIG. 1 illustrates a top-down view of a spiral tube support apparatus 1 showing a top or inner entry point 2 for tubing that goes clockwise through the spiral channels, for example, from the central shaft 4 out. The outer exit point of flow tubing is at 3. This is also visible at 17 in FIG. 2B, at the bottom of the spiral tube support 1. In the embodiment shown herein, the tubing enters the central shaft 4. Four curved radial channels 5 are shown; but the invention is not limited to specific number of radial channels 5. The radial channels 5 may be curved at one or both ends in accordance with this invention. Prior art inventions contained straight radial channels 5 which caused crimping of the tubes and as a consequence, impeded solvent flow, see WO 2009/073746. Tubing could be routed in a counterclockwise fashion in accordance with the invention. The spiral direction from center outwards can be counterclockwise and the radial channels can have, an "S" configuration.

The embodiment illustrated in FIG. 1 contains a cross-section of the improved spiral tubing support apparatus 1. Tubing can be routed through the radial channels 5 that are curved. The curvature aligns the tubing to enter the appropriate spiral channel to form the interweaved spirals of tubing. The spiral tube support 1 contains four interweaved spirals per layer. Tubing can be laid from the bottom of the frame and can be placed in a counterclockwise direction in the channel. Tubing is then passed, across the radial channel at 9 o'clock where it is guided to fit into the channel that is one in from the outside. At point 6 o'clock, the tubing crosses the radial channel into the channel that is to two channels in from the outer circumference. At point 3 o'clock, the tubing goes into the channel that is three channels in from the edge and so on. When the tubing crosses the radial channel near point 3, the tubing goes into the channel four rows in from the outer edge. This is repeated around the rotor until the tubing comes to the center and then is routed out the radial channel 5 located at 9 o'clock to the edge and then follows the channel along the edge and at 6 o'clock crosses the next radial channel into the channel one in from the edge as before until it reaches the center and out the next radial channel 5 again. When the tubing has reached the top at the center, it is routed out an access port to the top and connected to the tubing that goes into the center shaft.

The winding of tubing in a rotor of interest can utilize a radial channel, if present. As a rotor may not include a radial channel, tubing winding need not involve use of a radial channel even if present. Also, as taught herein, winding can be in either the clockwise (CW) or counterclockwise (CCW) direction, with a suitably configured rotor, as tubing direction and rotor rotation direction can be varied to enable and to maximize separation of a molecule or entity of interest.

Figure 2A:
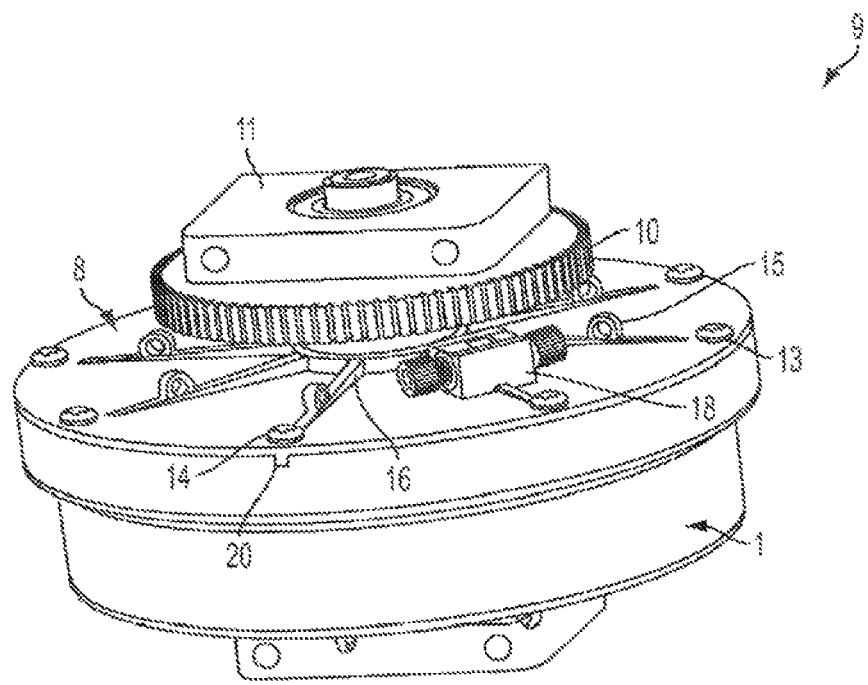
FIG. 2A is a side view of the assembled rotor with the gear and bearing blocks on the top and bottom of the spiral tubing support.
Figure 2B:
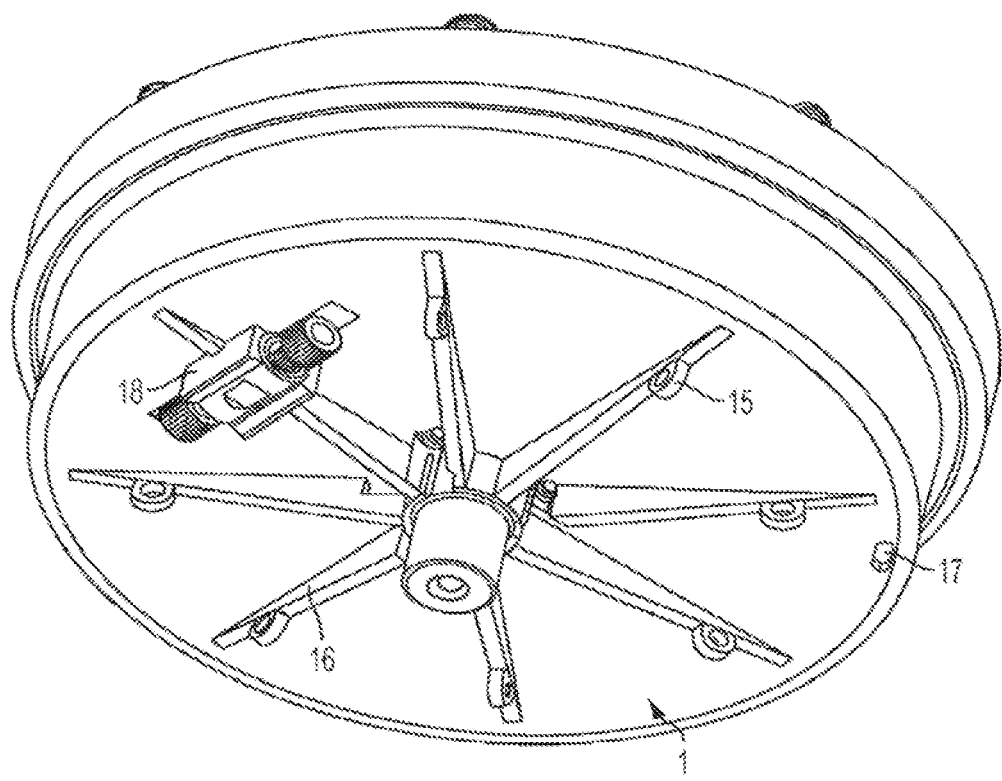
FIG. 2B is a bottom view of the spiral tube support.

As the direction of winding of the tubing is optional as a design choice, those parameters can be used for the separation of interest. A rotor of interest will have a suitably curved optional radial channel and with suitably oriented spiral channels or grooves. The channels or grooves are voids in the first surface which are configured and shaped to accept and to seat a tubing. Thus, at the center, the tubing can be guided into a radial channel and extends through the radial channel to the periphery of the first surface. The tubing is routed to the channel at the edge of the spiral tube support and passes into the channel that is one in from the edge. The tubing is routed into the channel that is two in from the edge and so on. When the tubing reaches the central shaft region, the tubing is routed through another radial channel to the outer edge and follows the spiral channels across the radial channel curving inward to the center inner entry area and out another radial channel until it reaches a final channel along the outer entry point area along the edge from which the tubing is routed through spiral channels until it reaches the center shaft area. The tubing passes through an exit or an access port in the cover where it is connected to flow tubing, for example, at a compression screw union (see, for example, FIGS. 2A and 2B where a compression screw union is depicted as seated in a snap lock means). The tubing enters the spiral tube support shaft (for example, as shown in FIGS. 1, 2A and 2B), and together with the tubing from the other entry from the spiral tube support can exit and enter the central axis shaft.

In general, the tubing is oriented in the spiral path that skips every three channels and returns to the outer region. The tubing in the radial channels may be pressed into a walled first surface space to accept plural layers of spirally oriented tubing, that is, to fit more layers in the frame. The flow of solvent is through the tubing and the lower or heavier phase of a two-phase solvent system are introduced from the inner entry point. Alternatively, the upper or lighter phase of a two-phase solvent system can be pumped via the outer entry point with the appropriate orientation of the spiraling on the rotor, and hence, the tubing, and the appropriate direction of rotation by the centrifuge.

Hence, a single tubing can be configured to form a series of interweaved spirals. For the purposes of the invention, interweaved is considered synonymous with interleaved, and also is synonymous with having a series of spirals in register or where a series of spirals is nested. The rotor contains two access points for ingress and egress of the tubing from the rotor of interest. Moreover, to enhance the flow path, the instant rotor enables a stacking of layers of interweaved spiral layers. Hence, a rotor can contain two layers, three layers, four layers, five layers, six layers, seven layers, eight layers, nine layers, ten layers, eleven layers, twelve layers, thirteen layers, fourteen layers, fifteen layers and so on of interweaved, nested spirals of tubing. The tubing can be wound from the bottom in a counterclockwise direction. The individual layers of interweaved spirals can be set or packed into the rotor body using a dedicated pressing tool with one or a plurality of rigid portions or projections that are shaped to fit into a radial channel, into a spiral channel or both.

At the periphery of the apparatus shown in FIG. 1, a series of holes 6 are shown. One or more the holes 6 may serve as a place for weights to help balance the spiral tube support. The term "weight" as used herein refers to any object with mass. Alternatively, one or more of the holes 6 may be used to attach a top 8 (see FIG. 2A) to the spiral tube support 1, for example, with a threaded hole 7 and a screw. The holes 6 need not be in a circular or cylindrical shape nor must they be located at or near the periphery of the device.

FIG. 2A shows a side view of the assembled spiral tube support or rotor 9 with the support 1 and a corresponding top 8. The top 8 is beneath a gear 10 and bearing block 11 for integration into a CCC apparatus and to generate planetary rotation. One or more gears 10 and one or more bearing blocks 11 can be varied in shape or position from those shown in FIG. 2A. The top 8 contains a hole near the center through which tubing passes to loops 15 on the surface of the top 8 and attaches to flow tubing that enters the central shaft 4 of FIG. 1. Similar to the tube support 1, the top 8 contains one or more holes 13 that can be circular in shape. One or more of the holes 13 may serve as a place for weights to help balance the assembled spiral tube support 9. Alternatively, one or more of the holes 13 may be used to attach the top 8 to the spiral tube support 1, for example, with a screw 14. The holes 13 need not be in a circular or cylindrical shape nor must they be located at or near the periphery of the device. Likewise, the holes 6 and 13 may align with each other for the placement of weights and for attachment means. The top 8 may be attached to the spiral tube support 1 by a variety of means including, but not limited to, one or more of the following: (1) one or more latches, (2) one or more bolts, (3) one or more snaps, (4) one or more clips, (5) one or more notches or other interlocking means 20, (6) one or more central spaces through which a shaft may be placed, (7) one or more threads which may be used to attach an opposing surface, or (8) any known locking mechanisms, as well as combinations thereof, wherein a combination includes having more than one of the eight types or a form which combines two or more functions. For example, a screw can be used as the attachment means. The top 8 may also contain threads which screw into the spiral tube support 1 as another means of attachment. Likewise the same variety of means of attachment may apply to attaching the spiral tube support 1 to the top 8. As shown in FIG. 2B, the tube support also includes a tubing access port, 17.

Another improvement over the prior art is the inclusion of one or more loops 15 and one or more retainer supports 16 shown in FIGS. 2A and 2B on the spiral tube support 1 and the top 8. The loops 15 may hold flow tubing. Both the loop 15 and the retainer support 16 may be spaced around the lower surface of the spiral tube support 1, the upper surface of the top 8 or both the spiral tube support 1 and the top 8. It is not necessary to have the loops 15 directly attached to the retainer supports 16. One could also use a shape other than a loop 15 to hold the flow tubing in a manner consistent with this invention. The retainer support 16 in the present embodiment appears in the shape of a wedge whereby the narrowest part of the wedge is oriented toward the periphery of the spiral tube support 1, the top 8, or both and the widest part of the wedge is oriented toward the center of the spiral tube support 1, the top 8, or both. Both the shape and spacing of the retainer support 16 may be altered from the present form in accordance with this invention. The ability to reposition the loops 15 is an improvement over the prior art by allowing one to: (1) avoid crimping the tubing, (2) avoid sharp edges that could abrade tubing, (3) avoid moving parts, and (4) have easier access when the assembled spiral tube support 9 is in the centrifuge. The advantage of the retainer support 16 is to add strength to the spiral tube support 1 and top 8 without adding much weight to either surface.

FIGS. 2A and 2B illustrate another improvement of a spiral tube support 1 and a top 8 wherein one or more compression screw unions are present. The compression screw union can be attached to the spiral tube support 1 and the top 8 by a snap lock 18. The purpose of this modification is to connect the internal tubing which is present in the spiral tube support 1 with flow tubing that has a different inner diameter. The flow tubing exits the spiral tube support 1 and goes through the shaft and out the bottom of the assembled spiral tube support apparatus 9 to the central solar axis shaft.

Figure 3:
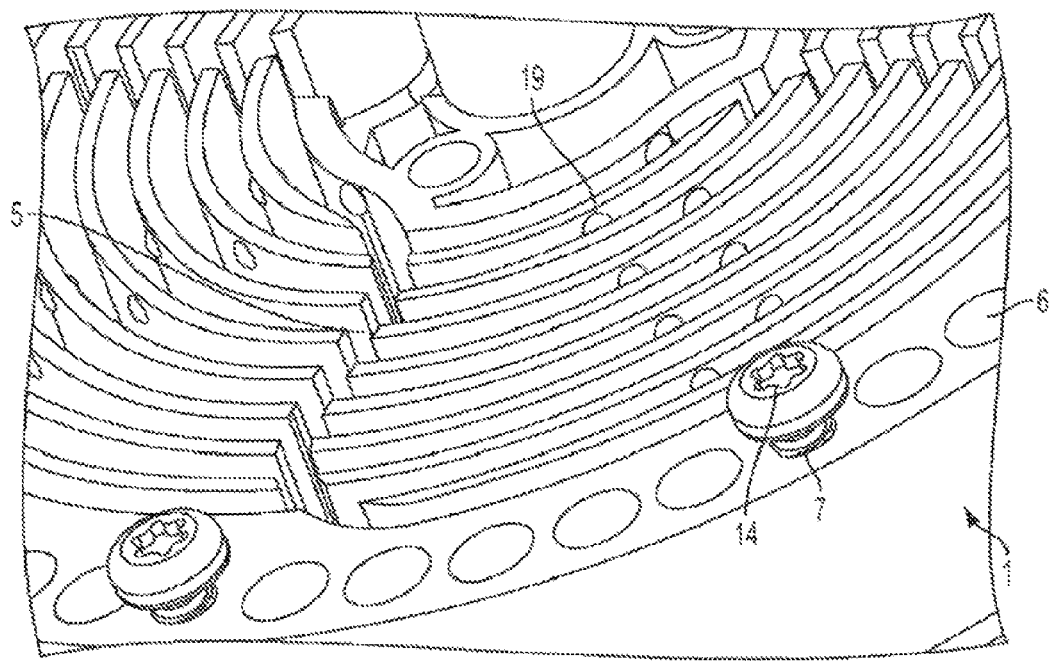
FIG. 3 is a close-up view of the spiral tubing support without the top.

In another embodiment, shown in FIG. 3, small protrusions 19 have been added to the surface of a spiral tube support 1 within the channels or grooves used in countercurrent chromatography. In prior inventions, the lack of such protrusions 19 hindered the routing or winding of tubing in the spiral tube support 1. The present invention restricts the general movement of tubing in or out of the spiral grooves, making the process of routing tubing through a spiral tube support 1 much easier and faster compared to the prior art.

In another embodiment, the assembled spiral tube support 9 is designed using a computer-assisted design (CAD) algorithm. The use of CAD to design the assembled spiral tube support 9 is not necessary for the purposes of this embodiment; but represents a convenient means of producing a design in accordance with the invention. A CAD-based design is advantageous over the prior art in that design changes can be accommodated. For example, the width of the spiral tubing can be varied to accommodate a tubing of a particular diameter. The width of each spiral channel can be between 0.5 mm and 10 mm, between 1 mm and 9 mm, between 2 mm and 8 mm, between 3 mm and 7 mm, between 4 mm and 6 mm, 5 mm, 2.5 mm, 3.5 mm and so on. The radial channels can have the same dimensions. The invention as exemplified in FIGS. 2A and 2B is cylindrical in shape with an approximate diameter of 17.5 cm and a height of approximately 7.3 cm. The shape and dimensions can be varied to accommodate any centrifuge type. The spiral tube support 1 comprises spring walls of the channels or groves, and radial channels 5 that come to the center and that may or may not be curved at one or both ends as illustrated in FIG. 1.

FIG. 1 depicts four curved radial channels 5. However, the tube support 1 can be manufactured with one or more straight or curved radial channels 5. Each radial channel 5 can have a width between 0.5 mm and 10 mm, between 1 mm and 7 mm, between 2 mm and 5 mm, between 3 mm and 4 mm, for example, or suitable scaled for separation involving larger volumes. The spiral channels or grooves can have the same size dimensions, which as mentioned, can be varied as a design choice depending on the scale of separation. Thus, the spiral channels and optional radial channels can exceed the sizes noted above to enable separation of larger volumes. Hence, the channels can be sized in centimeters, decimeters, inches and so on. It is also conceivable that a spiral tube support 1 could be constructed without a top 8. A preferred embodiment also contains small protrusions 19 on the surface of the spiral tube support 1 in the spiral channels to help with routing tubing.

The spiral tube support 1 and the top 8 can be formed from a variety of materials including, but not limited to, one or more of the following: (1) nylon polymer, (2) plastic, (3) polytetrafluoroethylene (Teflon®), (4) polyvinyl chloride, (5) polystyrene, (6) polyamide PA-220, (7) photopolymer, (8) FullCure® material, (9) Polyjet 3D Printer® material, (10) monomeric powder, and (11) a particulate comprising a metal or a metal composite. The aforementioned materials can be used to create a hard surface. To create a flexible structure a material such as Tango Black which is provided by Polyjet 3D Printer® may be used. The advantages of using an easily formed material are that a spiral tube support 1 or top 8 may be quickly and cheaply made and design changes can be easily accommodated. The prior art teaches the construction of spiral tube supports by drilling the spirals out of metal which is substantially more laborious to manufacture than the present invention. The present method of manufacturing the assembled countercurrent chromatography apparatus 9 encompasses the possibility that metal becomes amenable for use in a rapid prototyping machine as described next.

In one embodiment, the material used in the design is formed using a three-dimensional prototyping machine. The three-dimensional prototyping machine can use a variety of processes to form the tube support 1 or top 8 such as a laser sintering or ultraviolet irradiation. A person having ordinary skill in the art would appreciate that the spiral tube support 1 or top 8 may be formed in accordance with the invention using a process other than laser sintering or ultraviolet irradiation. Examples of a machine that can be used to form the material for the design of the spiral support include, but are not limited to a Sinterstation 2300 plus, Objet Geometrics, Inc. Eden 500V, or an EOS Precision.

Another improvement over the prior art is that the manufactured spiral tubing support 1 is compatible with any known flexible tubing including, but not limited to: (1) Teflon®, (2) fluorinated ethylene propylene, (3) silicone, (4) stainless steel, (5) Tygon®, (6) crenellated, (7) convoluted, (8) any commonly used flexible tubing, or (9) any tubing that includes a combination of any of the aforementioned materials. The tubing can also be manually or mechanically pressed in cross-presses or twisted. Because the device may accommodate a variety of channel sizes, tubing may have any virtually any diameter. In the past, it has been difficult to wind tubing into the spiral channels of a countercurrent chromatography apparatus. The same method of manufacturing the spiral tube support 1 and top 8 may be used to create a tool which can in turn be used to guide or push down tubing into the radial channels 5. This flattening out of the tubing allows more layers of tubing which can provide for greater separation of a test sample. Additionally, such a configuration disrupts laminar flow of the solvent.

The manufactured apparatus or a prior art countercurrent chromatography apparatus with the improvements described herein may be used to separate one or more biological materials and chemical substances. Biological material includes large molecules such as DNA, a polynucleotide, an oligonucleotide, a protein, a polypeptide, an oligopeptides, a polysaccharide, an oligosaccharide, a lipid, combinations thereof and so on. Whereas the prior art has been largely limited to small molecules, the present assembled spiral tube support 9 is capable of separating or purifying both small and large sized molecules. The invention is capable of holding specialized solvent systems, such as two-phase aqueous polyethylene and salt solutions as well as two-phase heavy alcohol aqueous solutions, which can purify large biological materials.

The CCC device and the instant rotor configured for use therein are readily amenable to scaling to accommodate separation of large volumes of liquid medium, such as a cell lysate or spent culture medium for molecules contained therein, such as polypeptides, oligopeptides, polynucleotides, oligonucleotides, polysaccharides, oligosaccharides, lipids, combinations thereof and so on.

Use of a rotor of interest is as known in the chromatography art as a rotor of interest can be configured for use in any chromatography device. Hence, a rotor of interest is loaded with tubing connected to suitable reservoirs or buffers, solvents and the like to provide stationary and mobile phases, and place in a chromatography apparatus, such as, a centrifuge, such as a planetary centrifuge. Sample is applied via the tubing and the centrifuge fun to provide the appropriate rotation of the rotor. Fractions are collected for further processing and/or analysis. The stationary phase can be displaced from the tubing by known means of flushing, such as, using a buffer, a solvent, or a gas.

The invention now will be exemplified in the following non-limiting examples.

EXAMPLES

Prior work using a spiral tube support apparatus in separations of small molecules and peptides elucidated the means of use or elution modes for each mobile phase. Tubing wound in a clockwise direction from the center or top can result in the stationary phase being retained in the conditions summarized in Table 1. The non-polar solvent systems used primarily for small molecules have different stationary phase retentions for the elution modes because of different hydrodynamic properties. Thus, the method of use of the subject spiral tube support apparatus is different with respect to polar solvent systems which have heretofore been difficult to use in countercurrent chromatography. The top of the spiral tube support can be the inner terminal into which the lower phase is introduced and the bottom of the spiral tube support can be the outer terminal into which the upper phase is pumped when used as the mobile phase. The inner terminal is the head when the rotation is clockwise or in the same direction as the winding direction of the spiral. The outer terminal is the tail under these conditions. The head and tail ends are reversed when the rotation is counterclockwise. The inner terminal becomes the tail when the rotation is counterclockwise. There can be high retention of the stationary phase under those conditions. The same elution modes can be used with the two-phase aqueous solvent systems ("TPAS"), such as polyethylene glycol/phosphate solutions. Table 2 lists the results of using those solvent systems with the high stationary phase retentions obtained for protein separation.

Operating parameters for the solvent systems used in exemplified experiments to purify proteins and fractionate lysates are shown below. The compositions of the TPAS can be modified to contain different MW polyethylene glycol ("PEG") and the salts can be of differing pH. Other additions, such as high MW dextrans may be added as well. Trifluoroacetic acid (TFA) can be used. The last solvent system listed in Table 2 uses a heavy alcohol n-butanol with a moderate concentration of aqueous phosphate buffer in the elution mode with the aqueous phase mobile to isolate proteins from lysates. Those conditions will not denature the proteins. Other heavy alcohols such as sec-butanol and other salts, such as NaCl, ammonium acetate, etc. can be used.

Example 1

The spiral tube support frame was built by the laser sintering technique using a Sinterstation 2300 plus rapid prototyping machine that performed the process of 3-D (dimensional) printing. The rapid prototyping machine formed the 3-D shapes of the spiral tube support and top designed by CAD. That was done by laser hardening of a monomeric powder, EOS Precision polyamide PA220. One and also three spiral tube support apparatuses were formed at the same time in the printer. The powder is layered in the chamber and a laser moves over the surface in the programmed pattern hardening the shape as it hits the surface. Then another layer of powder in applied with a spreader. Hence, multiple layers comprise the support 1 and top 8 when made as provided herein. The shape is built up from the bottom. When the form is complete, it is lifted out and washed with water to remove loose powder. The resulting hard white nylon composite rotor is stained or colored with a chemical resistant paint. The top was prepared using the same method of manufacturing as the spiral tube support and in addition a coating of Teflon® was applied to the underside of the top to prevent abrasion of the tubing in the assembled apparatus. A pressing tool was made by the same laser sintering process. This consists of a 15 cm diameter disk with a 2 cm center hole that fits over the shaft with four curved 5 cm extensions that fit into the radial grooves of the spiral tube support apparatus. Tubing, FEP SW #114 (Zeus Co.) 1.6 mm ID, 2.4 mm OD, was wound in the spiral tube support from the bottom and after every three layers, the tubing was pressed with the pressing tool with moderate pressure and held with clamps for 15 min. After that process, about 10 layers of the tubing fit to give a total volume of 135 ml capacity. The tubing in the assembled spiral tube support apparatus was filled with water. The apparatus was suspended by tubing from a screw inserted into the center shaft and weights were added to level the rotor. The weights are short metal bars (approx 2 cm long) inserted into the holes around the perimeter of the rotor and held in place with epoxy glue. The tubing from inside the rotor was connected to two pieces of flow tubing with nuts, ferrules and a union outside the bottom and on the cover to 0.8 mm ID, 1.6 mm OD PTFE flow tubing that went through the center axis shaft to the top of the planetary centrifuge and was clamped. The inflow tubing was connected to a sample loop which was connected to a solvent pump and the outflow tubing was connected to a fraction collector.

A 7.3 cm high and 17.5 cm OD spiral tube support and cover (dimensions without the gear) was constructed, placed and used in a Centrichrom planetary centrifuge and another rotor of the same size was used in a P.C. Inc. planetary centrifuge. The examples of experiments described herein were performed with this rotor in the Centrichrom instrument. The rotor in the centrifuge is balanced with a shaft opposite with weights. Additionally, a set of three rotors (10.4 cm high and 10.8 cm OD) were mounted in series on three separate planetary shafts with interconnected flow tubing in a Pharma-Tech Research Corporation planetary centrifuge and utilized in experiments. Finally, two rotors were built and mounted on a single shaft with tubing connected by a union. These rotors of dimensions 9 cm deep and 17 cm OD were built to mount in an instrument made by Shimadzu Corporation.

Example 2

This example illustrates the use of the spiral tube support to separate three peptides shown in Table 3. The 20-mer has a sequence identical to that of the 18-mer except that there is an additional W residue, and an H residue is substitute with an A in the 20-mer. The peptides were separated in the solvent system composed of a 1:1 (v/v) solution of sec-butanol-1% trifluoroacetic acid ("TFA") in water with the lower aqueous phase as the mobile phase. Approximately 10 mg of each peptide was separated at a flow rate of 1 ml/min. Fractions were collected at two minute intervals and the elution profile for each peptide was determined by HPLC and absorption spectrophotometry.

Initial studies of the spiral tube support apparatus must be made to measure the stationary phase retention of the solvent systems to be used for peptides and proteins under the operating conditions. The heavy phase and light phase of a solvent system are retained differently depending on the direction of centrifugation, and the direction the tubing was wound in the spiral tube support. Generally, the most retention of the stationary phase is achieved when the heavier phase is introduced through the inner inlet (head-to-tail) and the lighter phase is pumped into the outer terminal (tail-to-head). Under these settings, the lighter phase is used as the mobile phase and the spiral tube support is rotated in a counterclockwise direction. The stationary phase retention is measured for each phase used as a mobile phase. This is done by following: (1) filling the coil with the stationary phase, (2) beginning the rotation of the spiral tube support apparatus, and (3) pumping the mobile phase through. The volume that comes off the apparatus between the start of rotation and the time at which solvent front comes through represents the excluded volume, $V_m$, after the establishment of the equilibrium. Subtracting $V_m$ from the total column volume, $V_c$, yields the stationary phase volume, $V_g$. The phase retention is the ratio of the stationary phase volume to the total volume, $V_s/V_g$. While the elution of mobile phase occurs, there is an increase in back-pressure. The back-pressure is dependent on the interfacial tension of the solvent system.

A determination of the partition coefficient, K, is made by dissolving a small sample into a solvent system, shaking the mixture, and measuring the concentration of the sample in both phases after separation of the phases. That provides the ratio of concentration in the upper to lower phase ($C_u/C_l$). The phase chosen as the mobile phase is that giving a partition coefficient of 1 to 2. The efficiency of a separation will be determined by use of the conventional gas chromatographic equation: $N=(4R/W)^2$. The theoretical plate or N is calculated from the shape of the peaks. R is the retention time or volume of the peak maximum and W is the peak width expressed in the same units as R. For preparative separations, the values of N may be up to 1000, but the more important relationship is resolution. Resolution between adjacent peaks is given by: $R_S=2(V_{R,2}-V_{R,1})/(W_1+W_2)$. Using that equation and substituting each solute retention volume by the following: $V_R=V_m+KV_s$. The $V_m$ term cancels giving: $R_S=2(K_2-K_1)V_s/(W_1-W_2)$.

The resolution is proportional to the $V_s$ and the difference between K's. From the high $V_s$ typical of countercurrent chromatography, high resolution is possible with N<1000. The resolution is measured in isocratic elution (no gradient) which is the case in countercurrent chromatography and can be adjusted by composition of the solvent system.

Typically, the sample is dissolved in a small volume (not more than 1/10 the total volume of the coil) of both phases and loaded onto the coil already filled with the stationary phase. The centrifugation is begun and the mobile phase is pumped at, for example, 2 ml/min. The effluent can be passed through a UV detector with the direction upwards through the flow cell for a mobile lower phase and downwards for a mobile upper phase to clear phase droplets. The chromatography is allowed to proceed for two to three column volumes during which time actions are collected. When the rotation is stopped, the contents are pumped or pushed out with nitrogen or helium pressure and fractions continue to be collected. If desired, for very slow eluting compounds, the mobile phase can be changed by altering the entry of the other mobile phase and allowing the compounds to elute through the other phase as a stationary phase. Between runs, the coil of tubing can be cleaned by: (1) rinsing with water, (2) rinsing with acetone, and (3) drying the coil with a nitrogen stream. Collected fractions can be analyzed by protein assay on aliquots of the fractions to determine the elution profile of the protein or peptide of interest. Proteins or peptides could also be identified by performing mass spectrophometry on the collected fractions. The fractions containing the pure compound, as analyzed by HPLC or PAGE, can be pooled and dried.

As stated earlier, K is defined as $C_u/C_l$. For each peptide shown in Table 3, the experimental K ($K_{exp}$) was calculated by dividing the concentration in the stationary phase ($C_s$) by the concentration in the mobile phase ($C_m$). The three peptides eluted in the order expected and the expected K and $K_{exp}$ values were relatively well correlated.

The peptides eluted as expected from their respective K values (Table 3). The data demonstrate the spiral tube support rotor closely approximates the theoretical prediction and that relatively large-sized molecules can be effectively separated using the new rotor.

Example 3

This example illustrates the ability of a plastic spiral tube support, constructed using three-dimensional printing and laser sintering, to separate a mixture of small molecules (defined as molecules with a MW<500). The small molecule compounds aspirin, salicylic acid, salicin, and naringenin were loaded in the solvent system composed of a 1:1 (v/v) solution of sec-butanol-1% TFA in water. The loaded mixture was then centrifuged at 800 rpm in the spiral tube support with a flow rate of 1 ml/min. Fractions were collected at two minute intervals until 50 fractions had been collected. After the $50^{th}$ fraction had been collected, the contents were extruded.

All four of the small molecules were separated and only aspirin and naringenin partially overlapped in their elution. The elution order matches the anticipated order based on the K values of the molecules. The stationary phase retention was 69%, which is high. The data demonstrate the utility of the improved spiral tube support in separating small molecules. The design can be easily scaled up for industrial process or scaled down for analytical application to mass spectrometry.

Example 4

The apparatus of interest can be used to separate proteins or other large molecules. In this example, the spiral tube support was made as described above and used to purify mouse uteroglobin. Mouse uteroglobin has a MW of 70 kDa and normally exists as a dimer but, in solution, a monomeric form of the protein can also accumulate. A separation was made in the spiral tube support to separate uteroglobin monomers from uteroglobin dimers. This was done by measuring the K value using HPLC and then separating the protein using countercurrent chromatography with the spiral tube support apparatus. PAGE analysis demonstrated successful separation of the protein monomers and dimers and a quantitative method of HPLC was employed to measure the respective K values. The heights of the peaks representing the monomer at 31.5 min. and dimer at 32.8 min. HPLC retention time, respectively, were measured and the ratios give different values for the concentration in the upper phase over that of the lower phase. The two protein peaks calculated to K values of 4.0 and 6.9 in PEG (1000) 12.5%-$K_2HPO_4$ 12.5%. The different K values mean that the two species could be separated with one or the other phase mobile. Since the numeric value is over two, the analyte would remain in the coil a long time, ultimately being eluted in approximately four to seven column volumes. Consequently, a run was performed for two column volumes and then the contents of the column were extruded and analyzed.

The lower (mobile) phase showed the appearance of the protein in the expected volume and a volume of selected fractions collected from the experiment were examined by PAGE. PAGE showed the separation of the uteroglobin monomers and dimers, thus demonstrating the apparatus and method of using the apparatus were successful in separating large biological material such as proteins. A PAGE run of the starting material showed the presence of the moue uteroglobin monomers and dimers running at approximately 5 kDa and 14.5 kDa, respectively.

Example 5

Figure 4A:
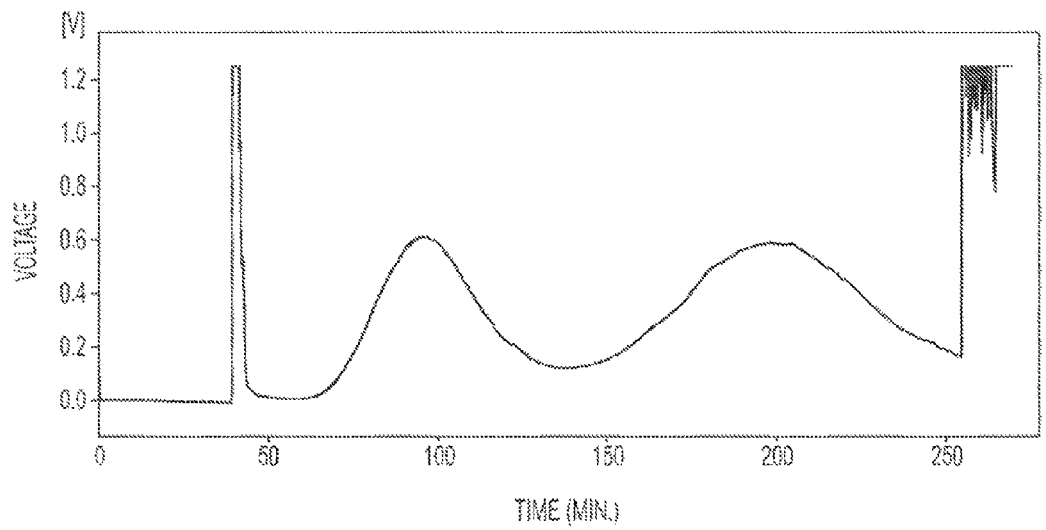
FIG. 4A is the elution profile for a mixture of proteins containing lysozyme and myoglobin that were separated using countercurrent chromatography.
Figure 4B:
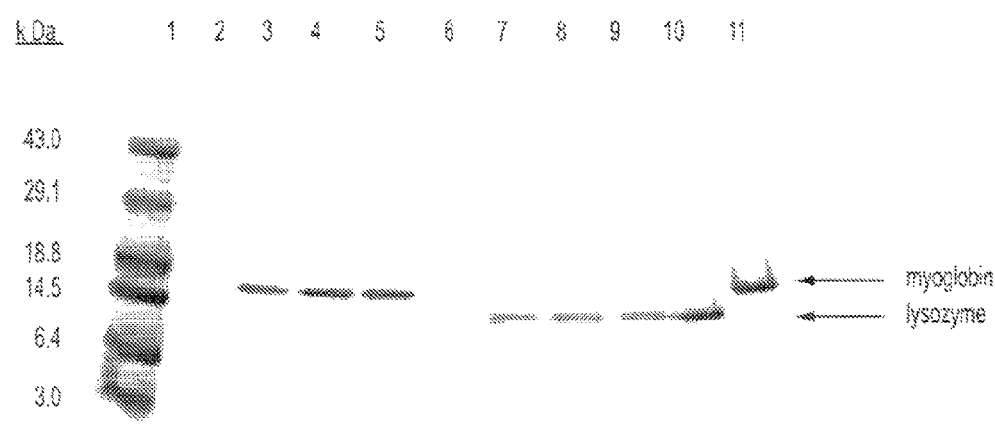
FIG. 4B is PAGE analysis of selected fractions from FIG. 4A showing successful separation of the two proteins.

This example further demonstrates the ability of the improved apparatus and methods of using said apparatus to separate large molecules. In this example, 31 mg lysozyme (14.4 kDa) and 24 mg myoglobin (17 kDa) were mixed and separated using the countercurrent chromatography apparatus and methods of use as claimed. A non-denaturing two-phase aqueous solvent system consisting of 12.5% PEG (MW 1000):12.5% $K_2HPO_4$ provides for a polyethylenerich upper phase and phosphate buffer-rich lower phase. The lower phase was used as the mobile phase at a flow rate of 1 ml/min. UV detection showed the elution of the solvent front at approximately 40 ml, indicating a stationary phase retention of 70%, followed by the two protein peaks that were baseline separated. FIG. 4A is a graph of the UV absorption (identified as voltage in the graph) for this particular experiment. FIG. 4B is PAGE analysis of the 100 minute peak (see lanes 3-5) and the 200 minute peak (see lanes 7-9). Lanes 10 and 11 are controls showing just lysozyme or myoglobin respectively. The data demonstrate the versatility of the countercurrent chromatography apparatus and method of use in purifying a mixture of large biological materials. The K values for myoglobin and lysozyme were 0.38 and 1.35 respectively and that corresponded to the order of elution.

Example 6

Another advantage of the countercurrent chromatography method and apparatus described herein is the ability to use a variety of solvent systems to separate a plurality of chemical or biological materials. In this example, the method and apparatus are used to separate proteins from crude lysate. Prior art inventions required other preparatory steps after cell lysis to perform the countercurrent chromatography (for example, centrifugation). A fusion protein expressed in *E. coli* was isolated after cell lysis, and no other chromatography or preparatory step, using the claimed spiral tube support apparatus and methods of use. A PEG solvent system as described in prior examples was used. The target fusion protein was separated from the bulk of host cell proteins and other cell debris and was sufficiently purified that it could be digested with a specific protease to release the target protein from the fusion protein. The digested fusion protein or peptide again was purified using the apparatus in an appropriate solvent system to separate the fusion tag from the protein product, starting fusion protein, and the protease.

Example 7

This example further illustrates the separation of a fusion protein, Tosyn 2-Insulin A, from crude lysate. Bacteria with the Tosyn 2-Insulin A fusion protein were grown in 4 L of SuperBroth. The pelleted bacterial cells weighed 87 g and were suspended in 435 ml of 20 mM $Na_2HPO_4$, 0.5 M NaCl, pH 7.2. The suspension was run twice through an Avestin Emulsiflex-C homogenizer at 10-15 Kpsi. The solution was centrifuged at 19,000×g for 30 min. at 4° C. Some of the supernatant was stored at −20° C. for later analysis. The target fusion protein has a MW of approximately 10 kDa.

The solvent system for spiral countercurrent chromatography was prepared by combining the following: 75 g PEG 1000, 75 g $K_2KPO_4$, and 450 g water in a 1 L Erlenmeyer flask (12.5% PEG:12.5% salt solvent system). The solution was stirred until the chemicals had completely dissolved. The solution then was transferred to a 500 ml glass separatory funnel where the solution was separated into approximately 240 ml of the upper phase and 300 ml of the lower phase. The crude lysate containing Tosyn 2-Insulin A was prepared by combining 9 g of thawed lysate (from the aforementioned homogenization), 1.5 g PEG 1000, and 1.5 g $K_2KPO_4$. After the chemicals had dissolved, the sample was centrifuged at 1000×g for 5 min. The clear part of the upper phase and clear part of the lower phase were combined into the sample loop for injection into the spiral rube support apparatus. The dark precipitate was left behind. The 12.5% PEG:12.5% salt solvent system serves to remove a substantial amount of cell debris and host cell protein and DNA.

The spiral tube support apparatus was placed in a planetary centrifuge and the tubing filled with the upper phase. To begin, the sample was centrifuged at 830 rpm the flow started at 1 ml/min and the sample injected into the flow line. The lower phase was eluted into the inner terminal with counterclockwise rotation. Fractions were collected every, two minutes. The solvent front or excluded upper phase from the spiral tube support apparatus came out at 44.5 ml or fraction 20. Stationary phase retention in the rum was 67%. At fraction 161, centrifugation was stopped. The contents remaining in the spiral tube support apparatus were pushed out with helium pressure and the fractions were collected.

Based on the peaks measured by absorption spectrophotometry, certain fractions were subjected to HPLC and PAGE analysis. According to PAGE, fraction 30 had many bands of lower MW and fractions 181 and 182 had many higher MW protein bands, including the 10 kDa target protein which appeared to be the smallest protein. The earlier fractions 177 to 174 had smaller amounts of proteins. The Tosyn 2-Insulin A fusion protein was separated from many proteins in the first large peak. By PAGE, the quantity of the late eluting protein appeared higher than the protein from the first eluting fraction even though the UV peak was higher.

In the separation above, the target protein was highly retained in the spiral tube support apparatus, so it was decided to elute in the reverse mode to observe if the protein would be better resolved. The same solvent system and same sample were prepared, but the spiral tube support apparatus was filled with the lower phase. The centrifugation was started and flow of the upper phase began. The upper phase was pumped into the outer terminal and the rotation was counterclockwise. The solvent front emerged at fraction 31 for a stationary phase retention of 59%. The protein that was retained in the other run was eluted after the solvent front and spread out in two major peaks. A very high UV absorbing fraction was at the end. PAGE showed the target protein present in the fraction 35 with other proteins and fractions 40, 50, and 55 also showed the presence of the protein in lower concentrations.

To observe the effect that higher MW PEG in the solvent system has on the separation, the same procedure as above was followed except that the solvent system and sample were made with higher MW PEG (MW 3350). The solvent front came out at fraction 39 with an excluded volume of 67 ml for a stationary phase retention of 50%. PAGE showed that the target protein was present at a significantly higher concentration than the higher MW proteins in faction 44 (and as compared to fractions 52, 56, and 112). Fractions 52 to 56 had the target protein and only one other significant protein. Fraction 112 had many different proteins and was removed from the target protein. This result seemed to remove more impurities from the fusion protein.

In summary, the tools of polymeric solvent systems can be varied by (1) composition with respect to MW of the polymer, (2) the pH of the aqueous salt, and (3) other inclusions that can be added to optimize the partition coefficient of a entity one seeks to purify. The solvent system can be applied in upper phase or lower phase mobile to maximally separate impurities. The instant invention is therefore a versatile method to isolate and purify entities, such as, macromolecules, such as, biomolecules.

TABLE 1

Measurement of $S_F$ in spiral tube support apparatus (PC, Inc. type) with 1% TFA/sec-butanol solvent system

| Elution mode<br>Flow at 1 ml/min, 800 rpm | % stationary phase retention | Direction of rotation |
| --- | --- | --- |
| L-i-T (T to H) | 73.6% | CCW |
| L-i-H (H to T) | 58.6% | CW |
| U-o-H | 64.8% | CCW |
| U-o-T | 55.7% | CW |

Lower phase inner terminal head ("L-i-H"),
lower phase inner terminal tail ("L-i-T"),
upper phase outer terminal head ("U-o-H") and
upper phase outer terminal tail ("U-o-T"),
"H" and "T" refer to head and tail respectively.
CW refers to clockwise and
CCW counterclockwise rotation.

TABLE 2

| Solvent system composition<br>Flow at 1 ml/min, 800 rpm | Elution Mode | % stationary phase retention |
| --- | --- | --- |
| TPAS-12.5% PEG (MW = 1000):12.5% K$_2$HPO$_4$ all by weight in water | L-i-T | 70.5% |
| | U-o-H | 59.3% |
| TPAS-12.5% PEG (MW = 3350):12.5% K$_2$HPO$_4$ | L-i-T | 72% |
| | U-o-H | 49.9% |
| TPAS-16% PEG (MW = 8000):6.25% K$_2$HPO$_4$:6.25% KH$_2$PO$_4$, Flow at 0.5 ml/min | L-i-T | 80% |
| n-butanol/0.1M K$_2$HPO$_4$, KH$_2$PO$_4$ (1:1) | L-i-H | 70% |

TABLE 3

| ID No. | Peptide Sequence | $K = C_u/C_l$ | Vol. at start of elution | $K_{exp} = C_s/C_m$ |
| --- | --- | --- | --- | --- |
| 6877 | 18-mer | 0.29 | 48 ml | 0.33 |
| 7131 | 20-mer | 0.91 | 104 ml | 1.22 |
| 507 | 14-mer | 2.4 | 164 ml | 2.17 |

All references cited herein are herein incorporated by reference in entirety.

The invention claimed is:

1. A method for using a countercurrent chromatography apparatus to separate one or more substances comprising: routing tubing through an inlet into a rotor for use in said apparatus comprising one or more first surfaces, each comprising a plurality of interweaved spiral channels; one or more tubing access ports; and one or more curved radial channels; routing said tubing through said interweaved spiral channels and then through an outlet in said rotor; providing a test sample containing said one or more substances; providing a solvent system; loading said test sample into said solvent system; placing said combined test sample and solvent system into said apparatus through said tubing; and providing rotation of said rotor in said apparatus to separate said one or more substances.

2. The method of claim 1, wherein said tubing has a non-uniform inner surface.

3. The method of claim 1, wherein said rotor further comprises one or more protrusions in said spiral channels to hold tubing in place.

4. The method of claim 1, wherein said rotor further comprises a space in which weights may be placed, a snap lock, a compression screw union, a loop, a retainer support or combinations thereof.

5. The method of claim 1, wherein said rotor further comprises a second surface, wherein said second surface is a top to said first surface.

6. The method of claim 5, wherein said second surface further comprises a tubing access port, a space in which weights may be placed, a locking mechanism, a loop, a snap lock, a retainer support or combinations thereof.

7. The method of claim 1, wherein said rotation is planetary.

8. The method of claim 1, wherein said solvent system is selected from the group consisting of a two-phase aqueous polyethylene and salt solution;
a two-phase heavy alcohol aqueous solution; a polyethylene glycol:K$_2$HPO$_4$ solution; and
a sec-butanol-trifluoroacetic acid solution.

9. The method of claim 1, wherein said one or more substances comprise a biological material.

10. The method of claim 9, wherein said biological material comprises a protein, a peptide or a DNA.

* * * * *